US00PP08055P

United States Patent [19]

Boerlage

[11] Patent Number: Plant 8,055

[45] Date of Patent: Dec. 8, 1992

[54] ROSE PLANT NAMED TINEKE

[75] Inventor: Herman H. Boerlage, Aalsmeer, Netherlands

[73] Assignee: DeVor Nurseries, Inc., Watsonville, Calif.

[21] Appl. No.: 651,751

[22] Filed: Feb. 7, 1991

[51] Int. Cl.[5] ..... A01H 5/00
[52] U.S. Cl. ..... Plt./14
[58] Field of Search ..... Plt./14, 23

[56] References Cited

U.S. PATENT DOCUMENTS

P.P. 3,610 9/1974 Fischer ..... Plt. 69

*Primary Examiner*—Howard J. Locker
*Attorney, Agent, or Firm*—Tilton, Fallon, Lungmus & Chestnut

[57] ABSTRACT

A new and distinct greenhouse rose particularly distinguished by its continuous and profuse production of large pure white flowers borne singly on long, strong, upright stems of a sturdy bush of medium height having abundant foliage of relatively large size.

1 Drawing Sheet

BACKGROUND OF THE NEW PLANT

My new rose plant originated as a hybrid seedling developed by my crossing a greenhouse stock plant identified as U.S. Plant Pat. No. K70 with pollen from a variety identified as unnamed seedling No. 3,610 at my nursery in De Kwakel, Holland. This particular seedling was selected for propagation because of its very large pure white bloom on a sturdy, upright plant having very favorable growth characteristics and original reproduction was done by tissue culture by Terra Negra B.V. at De Kwakel, Holland with such favorable results that further reproduction by means of cuttings through several successive generations at my nursery at De Kwakel, Holland which demonstrated conclusively that the novel characteristics of the parent seedling were carried from generation to generation and appeared to be firmly fixed. Propagation of this new plant is now being carried on at De Kwakel, Holland by tissue culture, grafting and cuttings with excellent results by each of these methods.

DESCRIPTION OF THE DRAWING

My new rose plant is illustrated by the accompanying photographic drawing which, in full color, shows a face view of a fully opened bloom showing its form and petal arrangement with the color rendition being as nearly true to that herein specified as is reasonably possible to obtain by conventional photographic procedures.

DESCRIPTION OF THE NEW VARIETY

The following is a detailed description of my new rose based upon observation of greenhouse grown plants at De Kwakel, Holland with the color designations being according to The R.H.S. Colour Chart published by The Royal Horticultural Society of London, England.

THE PLANT

Origin: Seedling.
Parentage:
*Seed parent.*—Nursery stock plant no. K70.
*Pollen parent.*—Unnamed seedling U.S. Plant Pat. No. 3,610 (unnamed).

Classification:
*Botanic.*—Rosa Hybrid.
*Commercial.*—Greenhouse Rose.
Form: An upright free-branching bush.
Growth rate: Vigorous, sturdy and upright.
Height: About 70 to 80 cm. after one year.
Main stem:
*Length.*—70 to 90 cm.
*Color.*—Yellow Green 146-A.
Foliage:
*Quantity.*—Abundant.
*Number of leaves.*—12 to 15 from last flower cut.
*Size.*—About 20 cm. long on both 5 and 7 compound leaves.
*Shape.*—Odd pinnate.
*Leaflets.*—Number: 5 and 7. Shape: Oval with denticulate margins. Size: About 8 cm. long. Texture: Semi-leathery. Aspect: Smooth and semi-glossy. Color: Upper side — Yellow Green 147-A. Under side — Yellow Green 147-B. Petiolule: About 1 to 2 mm.
Ribs and veins: Slightly depressed on upper side and rounded on the underside.
Thorns: This plant has no thorns.

THE BUD

Size: Large.
*Diameter.*—About 3 cm.
*Length.*—About 4 cm.
Shape: Ovoid, tapering and pointed.
Rate of opening: Slow.
Color of petals:
*When sepals first divide.*—Green White 157-D.
*When petals begin to unfurl.*—White 155-B.
Sepals:
*Number.*—5.
*Shape.*—Spreading with leaf pointed ends.
*Character.*—Branched and curled back when flowers open.
*Color.*—Inside — Yellow Green 148-C. Outside — Yellow Green 144-A.
Calyx:
*Shape.*—Funnel-shaped.
*Size.*—Large, about 4 cm. wide and 3 cm. long.
*Splitting.*—Calyx does not split.

*Aspect.*—Smooth.

Flower stem:

*Length.*—70 to 90 cm.

*Character.*—Slender and erect.

*Color.*—Yellow Green 146-B.

THE FLOWER

Blooming habit: Continuous and profusely, blooming freely under greenhouse conditions.

Size of bloom: Large.

*Diameter.*—About 10 cm.

*Depth.*—About 4 cm.

Borne: Singly on strong, upright stems.

Shape:

*When bloom first opens.*—Cup shaped with high center.

*When bloom matures.*—High center and very nicely imbricated.

Petalage:

*Number.*—50 to 55.

*Form.*—Wide spoon shaped with mucronate apex or cuspidate apex with curled back margins.

*Texture.*—Semi-leathery and soft.

*Aspect.*—Satiny.

*Color.*—Outer petals body — White 155-B and base of Green White 157-C. Reverse side body — White 155-C. Inside Petals body — White 155-B and base of Yellow 4-D. Reverse side — White 155-D.

Petaloids:

*Number.*—4.

*Size.*—1 to 2 cm.

*Color.*—White 155-D.

Persistence: The petals stay on the stem for more than 10 days.

Disease resistance: The flower has good resistance against mildew as observed at De Kwakel, Holland.

Fragrance: Slight.

Lasting Quality: Long lasting on the plant and as a cut flower.

THE REPRODUCTIVE ORGANS

Stamens:

*Number.*—170 to 180.

*Arrangement.*—Introrse.

*Anthers.*—Size: 2 to 3 mm. Color: Greyed Orange 164-C.

*Filaments.*—Length: 8 or 9 mm. Color: Yellow 2-D.

*Pollen.*—Color: Greyed Orange 164-C.

Pistils:

*Number.*—40 to 50.

*Styles.*—Length: 7 or 8 mm. Color: Greyed Orange 165-A.

*Stigmas.*—Color: Greyed Orange 164-C.

Character of the ovaries: Pear shaped.

THE FRUIT

Fertility: The fruit is fertile.

Shape: Pear shaped.

This plant most nearly resembles the variety Athena. However, the new variety is more pure white and the shape of the bud and flower is better than Athena.

I claim:

1. The new and distinct variety of greenhouse rose plant, substantially as herein shown and described, characterized by its profuse and continuous production of large pure white flowers borne on strong stems of medium length from a vigorous, upright bush having abundant foliage.

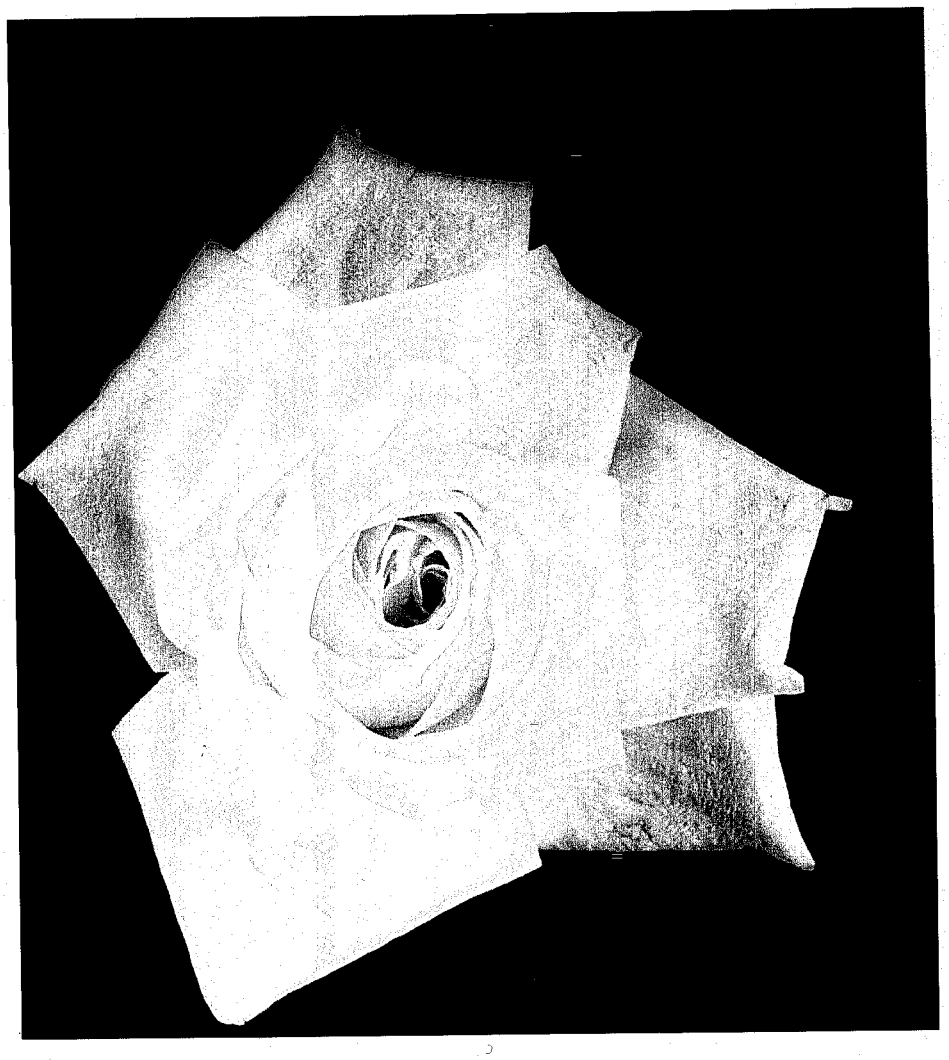

* * * * *